United States Patent
Kim et al.

(10) Patent No.: US 10,130,332 B2
(45) Date of Patent: Nov. 20, 2018

(54) METHOD AND APPARATUS OF DIAGNOSING CARDIAC DISEASES BASED ON MODELING OF CARDIAC MOTION

(71) Applicant: SAMSUNG ELECTRONICS CO., LTD., Suwon-si (KR)

(72) Inventors: Ji Yeon Kim, Hwaseong-si (KR); Hyong Euk Lee, Suwon-si (KR); Na Hyup Kang, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 593 days.

(21) Appl. No.: 14/450,541

(22) Filed: Aug. 4, 2014

(65) Prior Publication Data

US 2015/0045662 A1 Feb. 12, 2015

(30) Foreign Application Priority Data

Aug. 6, 2013 (KR) .................. 10-2013-0093098
Oct. 4, 2013 (KR) .................. 10-2013-0118804

(51) Int. Cl.
*A61B 8/08* (2006.01)
*G06T 7/00* (2017.01)
(Continued)

(52) U.S. Cl.
CPC .......... *A61B 8/0883* (2013.01); *A61B 8/0858* (2013.01); *A61B 8/5223* (2013.01);
(Continued)

(58) Field of Classification Search
CPC ... G06T 7/0083; G06T 7/0089; G06T 7/0014; G06T 2007/10132; G06T 2007/20124;
(Continued)

(56) References Cited

U.S. PATENT DOCUMENTS

2007/0014452 A1* 1/2007 Suresh ................ G06F 19/3437
382/128
2008/0103744 A1 5/2008 Rom
(Continued)

FOREIGN PATENT DOCUMENTS

JP 06-063025 3/1994
JP 2008-528099 7/2008
(Continued)

OTHER PUBLICATIONS

Adityo Prakosa et al., "Non-invasive Activation Times Estimation Using 3D Echocardiography", STACOM-CESC 2010, LNCS 6364, pp. 212-221.

*Primary Examiner* — Peter Luong
(74) *Attorney, Agent, or Firm* — NSIP Law (57) ABSTRACT

A method and an apparatus for diagnosing cardiac diseases based on a cardiac motion modeling are provided. The method may include applying physical characteristics of a cardiac motion to a 3D heart shape model, deriving a boundary condition by fusing the 3D heart shape model to which the physical characteristics are applied and a plurality of cardiac ultrasound images according to a temporal change, obtained to acquire a dynamic image, and diagnosing the cardiac diseases using a result of modeling that models the cardiac motion of the user using the boundary condition.

19 Claims, 8 Drawing Sheets

(51) Int. Cl.
*G06T 7/12* (2017.01)
*G06T 7/149* (2017.01)
*A61B 6/03* (2006.01)
*A61B 6/00* (2006.01)
*A61B 5/055* (2006.01)

(52) U.S. Cl.
CPC .......... *A61B 8/5261* (2013.01); *G06T 7/0014* (2013.01); *G06T 7/12* (2017.01); *G06T 7/149* (2017.01); *A61B 5/055* (2013.01); *A61B 6/032* (2013.01); *A61B 6/503* (2013.01); *A61B 6/5217* (2013.01); *G06T 2207/10081* (2013.01); *G06T 2207/10132* (2013.01); *G06T 2207/10136* (2013.01); *G06T 2207/20124* (2013.01); *G06T 2207/30048* (2013.01)

(58) Field of Classification Search
CPC . G06T 2007/30048; G06T 2007/10081; G06T 2007/10136; A61B 8/0883; A61B 8/5261; A61B 8/5223; A61B 8/0858; A61B 5/055; A61B 6/5217; A61B 6/503; A61B 6/032
See application file for complete search history.

(56) References Cited

U.S. PATENT DOCUMENTS

| | | |
|---|---|---|
| 2008/0319308 A1 | 12/2008 | Tang |
| 2010/0280352 A1 | 11/2010 | Ionasec et al. |
| 2011/0060576 A1 | 3/2011 | Sharma et al. |
| 2012/0259608 A1 | 10/2012 | Spilker et al. |
| 2013/0101187 A1 | 4/2013 | Sundar et al. |
| 2013/0197881 A1* | 8/2013 | Mansi ................ G06F 17/5009 703/2 |

FOREIGN PATENT DOCUMENTS

| | | |
|---|---|---|
| JP | 2009-545003 | 12/2009 |
| WO | 2008/047766 A1 | 4/2008 |

* cited by examiner

FIG. 10

METHOD AND APPARATUS OF DIAGNOSING CARDIAC DISEASES BASED ON MODELING OF CARDIAC MOTION

CROSS-REFERENCE TO RELATED APPLICATIONS

This application claims the benefit under 35 USC § 119(a) of Korean Patent Application No. 10-2013-0093098, filed on Aug. 6, 2013, and Korean Patent Application No. 10-2013-0118804, filed on Oct. 4, 2013, in the Korean Intellectual Property Office, the entire disclosures of which are incorporated herein by reference for all purposes.

BACKGROUND

1. Field

Embodiments of the following description relate to a method and apparatus for diagnosing cardiac diseases based on a cardiac motion modeling.

2. Description of the Related Art

Various modeling apparatuses and methods are used to diagnose cardiac diseases. According to one representative method, a doctor observes a cardiac motion through a cardiac ultrasound and assigns wall motion scores to cardiac motions according to segments to use the wall motion scores as an indicator of the cardiac motion. However, the wall motion scores are measured according to the subjective judgment of the doctor and therefore do not provide an objective indicator.

SUMMARY

Additional aspects and/or advantages will be set forth in part in the description which follows and, in part, will be apparent from the description, or may be learned by practice of the invention.

In an aspect, there is provided a method of modeling a cardiac motion, the method including generating a 3-dimensional (3D) heart shape model; applying physical characteristics of a cardiac motion to the 3D heart shape model, obtaining a plurality of cardiac ultrasound images according to a temporal change to obtain a dynamic image, deriving a boundary condition by fusing the 3D heart shape model to which the physical characteristics are applied and the plurality of cardiac ultrasound images, and modeling the cardiac motion of the user using the boundary condition.

The method may further include diagnosing cardiac diseases using a result of the modeling.

The 3D heart shape model may be generated based on a 2D image or 3D image capturing the user.

The 2D image or 3D image capturing the user may include a computed tomography (CT) image.

The applying may include selecting parameters reflecting the physical characteristics of the cardiac motion, and applying the physical characteristics of the cardiac motion to the 3D heart shape model using the parameters.

The physical characteristics may include at least one of a fiber orientation of a myocardium, a passive stress of the myocardium, and an active stress of the myocardium.

The deriving may include fusing the 3D heart shape model and the plurality of cardiac ultrasound images in consideration of a position change of feature points according to time in the plurality of cardiac ultrasound images.

The deriving may include searching for a displacement boundary condition of the boundary condition using the 3D heart shape model and cardiac ultrasound images being fused.

The boundary condition may include a displacement boundary condition and a load boundary condition.

The method may further include diagnosing cardiac diseases using a result of the modeling, wherein the diagnosing may include optimizing the selected parameters using the result of the modeling, acquiring distribution of myocardial motion information using the optimized parameters, and diagnosing the cardiac diseases using the distribution.

The optimizing may include evaluating the myocardial motion information acquired as a result of the modeling, and optimizing the selected parameters using a result of the evaluation so that the parameters reflect physical characteristics of the cardiac motion of the user.

The myocardial motion information may include a strain distribution of a myocardium and a stress of the myocardium.

The evaluating may include evaluating the myocardial motion information using a reference strain.

The reference strain may include cardiac motion information acquired from the plurality of cardiac ultrasound images.

The optimizing may include analyzing an influence of the parameters with respect to the reference strain, and optimizing the parameters using a result of the analysis.

In an aspect, there is provided an apparatus for diagnosing cardiac diseases, the apparatus including an application unit configured to apply physical characteristics of a cardiac motion to a 3-dimensional (3D) heart shape model, an obtaining unit configured to obtain a plurality of cardiac ultrasound images according to a temporal change to obtain a dynamic image, a derivation unit configured to derive a boundary condition by fusing the 3D heart shape model to which the physical characteristics are applied and the plurality of cardiac ultrasound images, and a modeling unit configured to model the cardiac motion of the user using the boundary condition.

The application unit may be configured to select parameters reflecting the physical characteristics of the cardiac motion and apply the physical characteristics to the 3D heart shape model using the parameters.

The derivation unit may include a fusing unit configured to fuse the 3D heart shape model and a plurality of cardiac ultrasound images of the user in consideration of a position change of feature points according to time in the plurality of cardiac ultrasound images.

The apparatus may further include a diagnosis unit configured to diagnose the cardiac diseases using a result of the modeling, wherein the diagnosis unit may include an optimization unit configured to optimize the parameters using the result of the modeling, and an acquiring unit configured to acquire distribution of myocardial motion information using the optimized parameters, and the diagnosis unit diagnoses the cardiac diseases using the distribution.

The diagnosis unit may further include an evaluation unit configured to evaluate myocardial motion information acquired from the result of the modeling, and optimizes the parameters using a result of the evaluation so that the parameters reflect physical characteristics of the cardiac motion of the user.

In an aspect, a method of modeling a cardiac motion is provided. The method includes applying physical characteristics of a cardiac motion to a 3D heart shape model generated using a first type of cardiac imaging, obtaining a plurality of temporally sequential cardiac images using a second type of cardiac imaging deriving a boundary condition by fusing the 3D heart shape model to which the physical characteristics have been applied and the plurality of sequential cardiac images, and modeling the cardiac motion using the derived boundary condition.

Other features and aspects will be apparent from the following detailed description, the drawings, and the claims.

BRIEF DESCRIPTION OF THE DRAWINGS

These and/or other aspects and advantages will become apparent and more readily appreciated from the following description of the embodiments, taken in conjunction with the accompanying drawings of which.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses, and/or methods described herein will be suggested to those of ordinary skill in the art. The progression of processing steps and/or operations described is an example; however, the sequence of steps and/or operations is not limited to that set forth herein and may be changed as is known in the art, with the exception of steps and/or operations necessarily occurring in a certain order. Also, description of well-known functions and constructions may be omitted for increased clarity and conciseness. Reference will be made in detail to the embodiments, examples of which are illustrated in the accompanying drawings, wherein like reference numerals refer to like elements throughout. The embodiments are described below to explain the present disclosure by referring to the figures.

Figure 1:
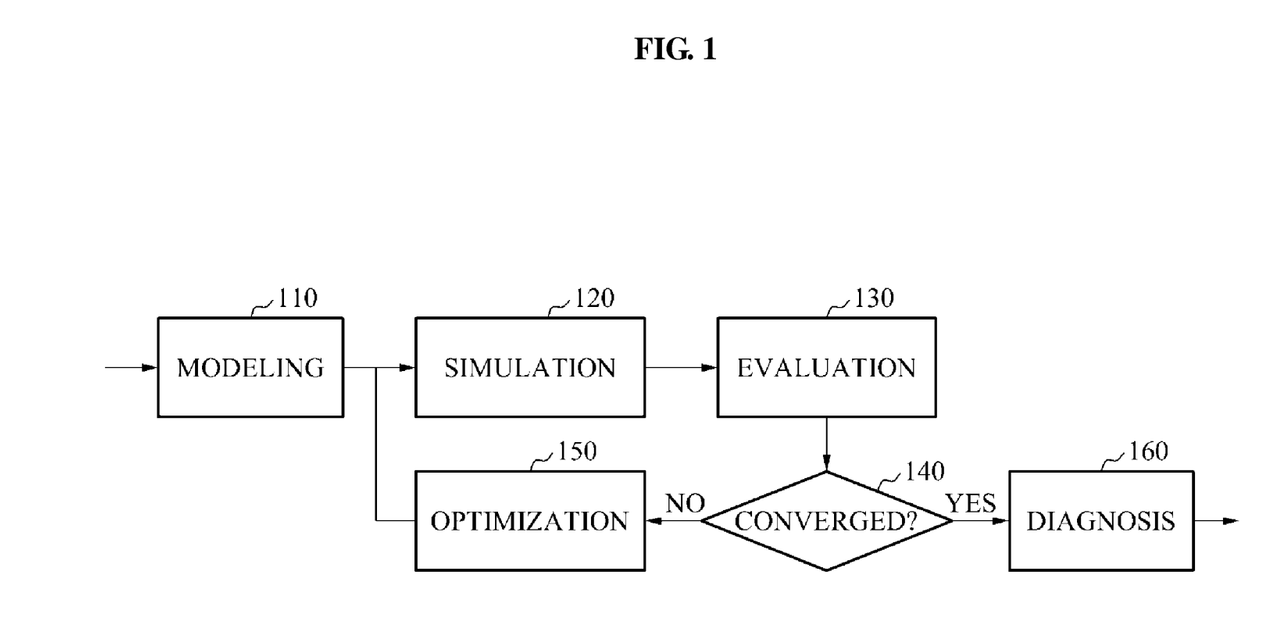
FIG. 1 is a diagram illustrating an overall operation concept of an example of a method of diagnosing cardiac diseases based on a cardiac motion modeling.

FIG. 1 illustrates an overall operational flow of an example of a method of diagnosing cardiac diseases based on a cardiac motion modeling.

In the cardiac disease diagnosing method according to an embodiment, myocardial motion information with respect to every part of a heart is acquired with cardiac motion modeling using a 3-dimensional (3D) heart shape model of a user and used for diagnosis of heart diseases.

The myocardial motion information may include information on a strain, that is, a degree of deformation of a myocardium, distribution of strains of the myocardium, and a stress of the myocardium.

Referring to FIG. 1, in 110, an apparatus for modeling a cardiac motion (hereinafter a "modeling apparatus") may generate the 3D heart shape model based on an image such as a magnetic resonance imaging (MRI) image or a computed tomography (CT) image related to the heart of the user. The 3D heart shape model produced based on the image of the heart of the user may be specialized for the user. The specialized heart shape model may be used to model a cardiac motion of the user.

The 3D heart shape model produced during the modeling 110 may reflect physical characteristics to be considered in the cardiac motion different from other organs. The physical characteristics may be referred to as "physical characteristics of the cardiac motion."

Different from other organs, the heart is made up of muscles called the myocardium. The physical characteristics may be varied according to orientation of fibers constituting the myocardium. Distinctive features of the heart with respect to other organs will be described in detail with reference to FIG. 3.

The physical characteristics of the cardiac motion may be parameterized. Therefore, parameters reflecting the physical characteristics of the cardiac motion may be applied to the 3D heart shape model produced during the modeling 110, so that operational characteristics of the heart and the like may be reflected in the 3D heart shape model. Here, adjustment of the parameters to fit the user may be performed in an optimization 150 that will be described later.

When the 3D heart shape model of the user is produced in the modeling 110, the modeling apparatus may model the cardiac motion of the user using the 3D heart shape model in 120.

In the modeling or simulation 120, the modeling apparatus may derive a boundary condition through fusion between heterogeneous images related to the heart of the user, and perform the modeling using the boundary condition. Here, the heterogeneous images refer to different kinds of images through which a 3D structure and a motion related to the heart of the user may be understood. For example, the heterogeneous images may include heterogeneously-obtained images or images obtained using varying techniques such as a 3D CT image and a cardiac ultrasound image.

The boundary condition relates to a method of processing boundary regions or boundary spots between two different images being fused. Fusion between heterogeneous images and derivation of the boundary condition through the fusion will be described with reference to FIG. 5.

In 130, the modeling apparatus may evaluate cardiac motion information of the myocardium, acquired as a result of the cardiac motion modeling.

During the evaluation 130, the modeling apparatus may verify and evaluate the cardiac motion information acquired through the modeling 120. The evaluation 130 is performed to evaluate whether the parameters reflecting the physical characteristics of the heart correctly reflect the cardiac motion information of the corresponding user's heart.

In 140, the modeling apparatus may determine whether an evaluation result converges into a predetermined value.

When the evaluation result converges into the predetermined value as a result of the determination 140, in diagnosis 160, the modeling apparatus may diagnose a cardiac disease of the user using the cardiac motion information acquired through the modeling 120.

When the evaluation result does not converge into the predetermined value as a result of the determination 140, in optimization 150, the modeling apparatus 130 may optimize parameters reflecting physical characteristics of an individual using a result of the verification and of the evaluation 130. For example, the optimization 150 may optimize the parameters selected in the modeling 110 for the user using the cardiac motion information acquired from the cardiac ultrasound image.

In the embodiment, the cardiac motion information, for example the distribution of strain, with respect to an entire part of the heart of the user may be acquired by repeating processes from the modeling 120 to the optimization 150 and may be used for diagnosis of cardiac diseases caused by an abnormal cardiac motion.

Figure 2:
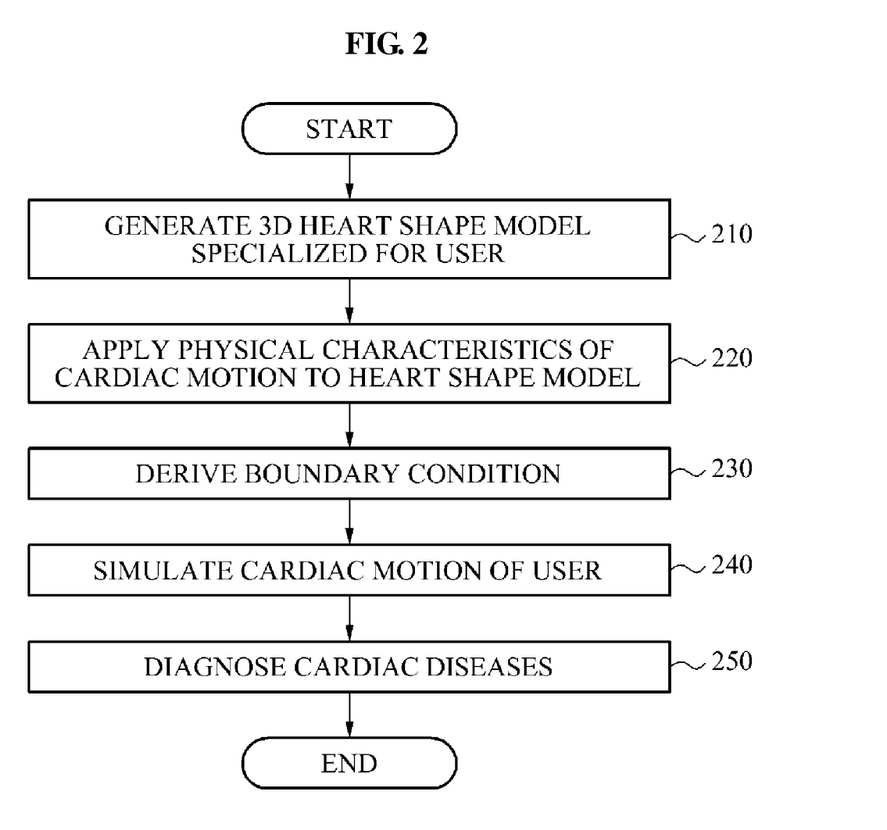
FIG. 2 is a flow chart illustrating an example of a method of modeling a cardiac motion.

FIG. 2 illustrates an example of a method of modeling a cardiac motion.

Referring to FIG. 2, in 210, a modeling apparatus may produce a 3D heart shape model personalized for a user based on a 3D CT image of the user. The 3D heart shape model may be generated based on a 2D image or 3D image capturing the user. Here, the 2D image or 3D image capturing the user may include a CT image. The method for producing the 3D heart shape model with the modeling apparatus will be described in detail with reference to FIG. 4.

In 220, the modeling apparatus may apply physical characteristics of a cardiac motion to the 3D heart shape model produced in 210. In 220, the modeling apparatus may select parameters reflecting physical characteristics of the cardiac motion, and apply the physical characteristics to the 3D heart shape model using the parameters. The physical characteristics may include at least one of a fiber orientation of a myocardium, a passive stress of the myocardium, and an active stress of the myocardium.

In 230, the modeling apparatus may obtain a plurality of cardiac ultrasound images according to a temporal change, to obtain a dynamic image.

In 240, the modeling apparatus may derive a boundary condition, by fusing the 3D heart shape model to which the physical characteristics generated in 210 are applied and the plurality of cardiac ultrasound images obtained in 230. The boundary condition may be applied to the 3D heart shape model produced in 210 to model the cardiac motion of the user.

For example, the method of fusing the 3D heart shape model and the plurality of cardiac ultrasound images obtained in 230, and the method of deriving the boundary condition by the modeling apparatus will be described in detail with reference to FIGS. 5 and 6.

In 250, the modeling apparatus may model the cardiac motion of the user using the boundary condition derived in 230.

In 260, the modeling apparatus may diagnose one or more different cardiac diseases using a result of the modeling of 240. The modeling apparatus may acquire the strain distribution of the myocardium of the user through the modeling result and may perform cardiac diagnosis using the strain distribution. The method of diagnosing the cardiac diseases by the modeling apparatus will be described in detail with reference to FIG. 8.

Figure 3:
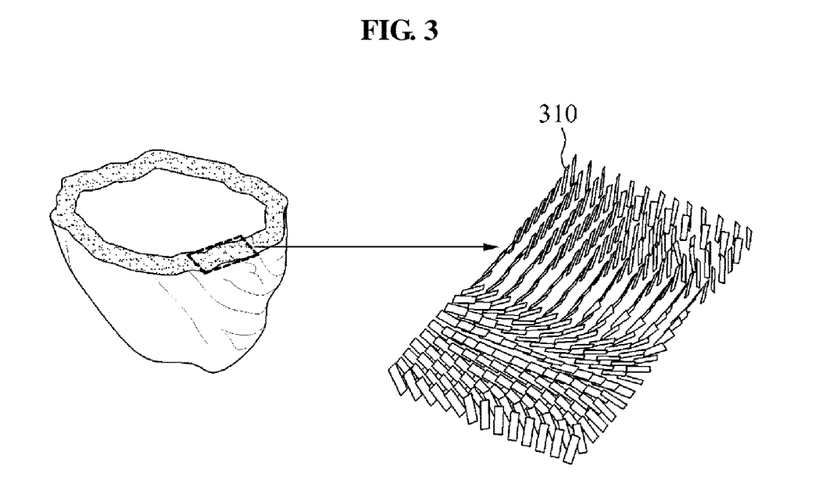
FIG. 3 is a diagram illustrating an example of characteristics of a cardiac motion to be modeled.

FIG. 3 illustrates an example of characteristics of a cardiac motion to be modeled.

Referring to FIG. 3, physical characteristics to be considered in relation to the cardiac motion are shown. The physical characteristics may be referred to as "physical characteristics of the cardiac motion."

In contrast with other organs, the heart is made up of muscles called the myocardium. The physical characteristics may be varied according to orientation of fibers 310 constituting the myocardium. In particular, since it is necessary to know the myocardial motion or the orientation of the fibers 310 while blood flows through left and right atria and ventricles, there may be other factors to be considered that are different from other organs.

Therefore, to consider the orientation of the fibers 310, a 3D heart shape may be modeled by dividing the heart into three layers and configuring a 3D mesh with respect to the respective layers. The 3D heart shape model according to the embodiment will be described by referencing FIG. 4.

Besides, the physical characteristics of the cardiac motion may include a passive stress which is a pushing or pulling force generated inside the myocardium when an external force is applied to the myocardium, and an active stress which is a force operating inside the myocardium without application of an external force.

The foregoing physical characteristics may be expressed by parameters. Therefore, the parameters reflecting the physical characteristics of the cardiac motion may be applied to the 3D heart shape modeled during modeling 110, so that operational characteristics of the heart are reflected to the 3D heart shape model.

Figure 4:
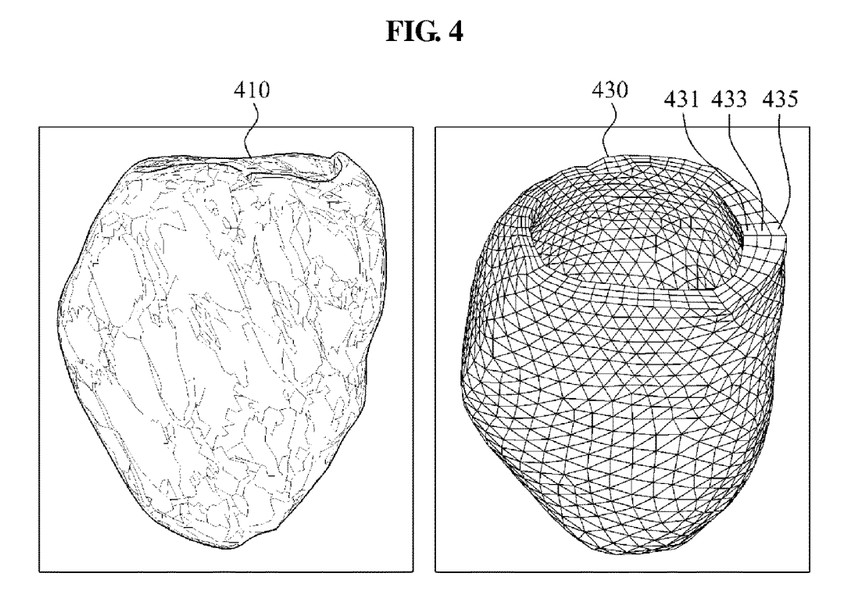
FIG. 4 is a diagram illustrating a 3-dimensional (3D) heart shape model produced in an example of a method of modeling a cardiac motion.

FIG. 4 illustrates a 3D heart shape model 430 produced in an example of a method of modeling a cardiac motion.

Referring to FIG. 4, a modeling apparatus according to an embodiment may generate the 3D heart shape model 430 using a medical image 410 in the form of a 3D volume. The medical image 410 is generated using a plurality of 2D images of a heart which is an object organ. Here, the medical image 410 of the 3D volume form may be generated from an MRI image and a CT image.

The 3D heart shape model may be generated as a 3D heart shape model specialized for a user using a heart region masked in the medical region 410 related to the user. Here, the modeling apparatus may reflect characteristics of a heart shape of the user using a volume mesh model of a preconfigured template organ. The template organ may be a 3D model selected to have a general shape of the actual corresponding organ.

The modeling apparatus according to the embodiment may form a surface mesh from the medical image 410 of the 3D volume form and then form the 3D heart shape model including an endo layer 431, a mid layer 433, and an epi layer 435 so that orientation of myocardium fibers are considered. In the 3D heart shape model 430 including a 3D mesh with the three layers, motions in the respective layers may be different from one another.

Figure 5:
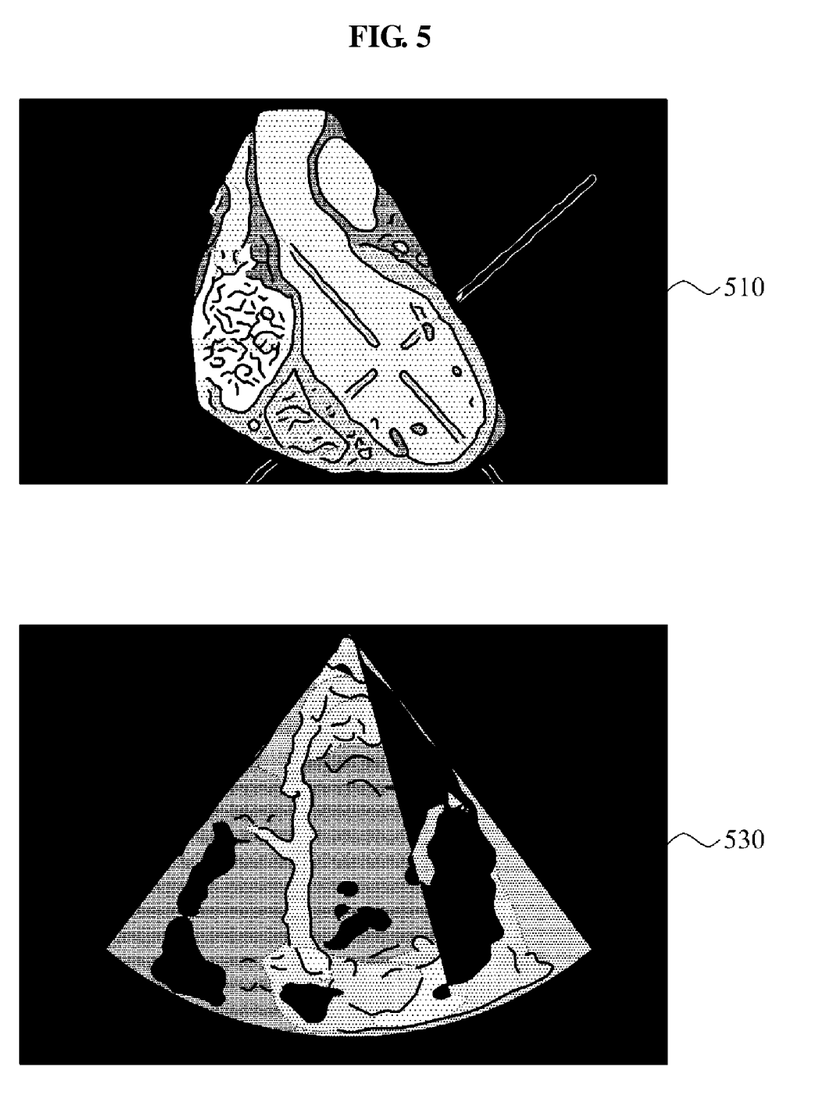
FIG. 5 is a diagram illustrating image fusion of heterogeneous images used for an example of a method of modeling a cardiac motion.

FIG. 5 illustrates image fusion of heterogeneous images such as heterogeneously-obtained images used for an example of a method of modeling a cardiac motion.

Referring to FIG. 5, a CT image 510 and a cardiac ultrasound image 530 related to a heart of a user are shown. The CT image 510 may show a 3D shape of the heart but not a motion of the heart. The cardiac ultrasound image 530 may show the motion of the heart but not the 3D shape of the heart. To this end, according to the embodiment, the different kinds of images may be fused and a boundary condition may be derived, so that characteristics of the shape and characteristics of the motion are reflected to the modeling.

The modeling apparatus may extract feature points from the CT image 510 and the 2D cardiac ultrasound image, respectively, and match the feature points of the CT image 510 and the feature points of the cardiac ultrasound image 530 to each other, thereby fusing the CT image 510 and the cardiac ultrasound image 530. The modeling apparatus may perform the fusion of a 3D heart shape model obtained from the CT image 510 and the cardiac ultrasound image 530, in consideration of a position change of the feature points according to time in the cardiac ultrasound image 530. The modeling apparatus may search for a displacement boundary condition using the 3D heart shape model and the cardiac ultrasound image 530 being fused.

Here, the boundary condition is used for processing boundary regions or boundary spots between two different images being fused. The boundary condition may be divided into the displacement boundary condition and a load boundary condition. For example, the displacement boundary condition may indicate a motion in which feature points of the heart slide on a diaphragm in the cardiac ultrasound image. That is, the displacement boundary condition may indicate a physical change of respective positions of a myocardium. The load boundary condition may refer to a force or pressure applied to the respective positions of the myocardium inside the heart. The load boundary condition may be expressed as a change in force applied to the myocardium as time passes when the heart periodically moves as shown by a graph of FIG. 6. The displacement boundary condition may also be called an essential boundary condition and the load boundary condition may also be called a natural boundary condition.

Figure 6:
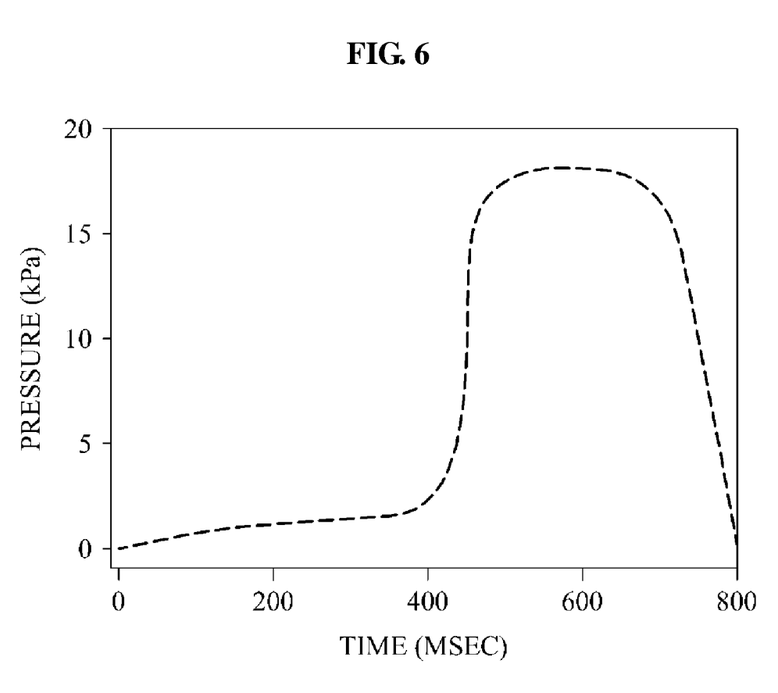
FIG. 6 is a graph illustrating a load boundary condition according to a change of a force applied to a myocardium as time passes in an example of a method of modeling a cardiac motion.

FIG. 6 illustrates a load boundary condition according to a change of a force applied to a myocardium as time passes in an example of a method of modeling a cardiac motion.

Figure 7:
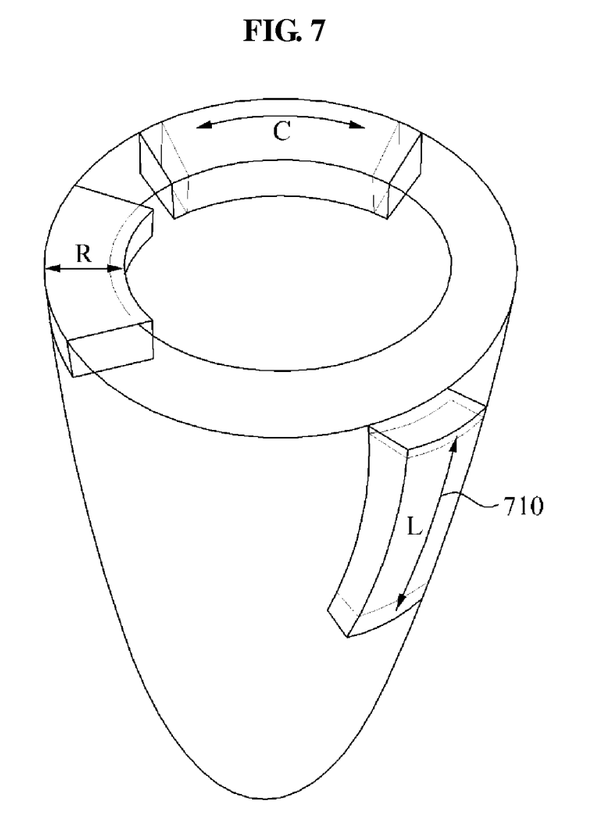
FIG. 7 is a diagram illustrating an example of a method of evaluating myocardial motion information acquired as a modeling result in an example of a method of modeling a cardiac motion.

FIG. 7 illustrates an example of a method of evaluating myocardial motion information acquired as a modeling result in an example of a method of modeling a cardiac motion.

Referring to FIG. 7, a modeling apparatus according to an embodiment may acquire a 2D cross section strain from a cardiac ultrasound image using a speckle tracking echo (STE) method. The STE method shows how cardiac structures transform during a cardiac motion period by tracking motions of speckles in the cardiac ultrasound image.

Here, a longitudinal strain L 710 of the 2D cross section strain may be relatively accurately acquired in comparison to strains of other directions, for example a radial direction R and a circumferential direction C.

Therefore, in the embodiment, evaluation with respect to the myocardial motion information may be performed by comparing the longitudinal strain L 710 with the myocardial motion information, that is, longitudinal myocardial motion information, acquired through the modeling. Alternatively, the modeling apparatus may perform the evaluation by comparing motion information with respect to an entire heart obtained from feature points of the heart or myocardium with the myocardial motion information.

The longitudinal strain thus used in verification and evaluation may be referred to as a "reference strain."

Figure 8:
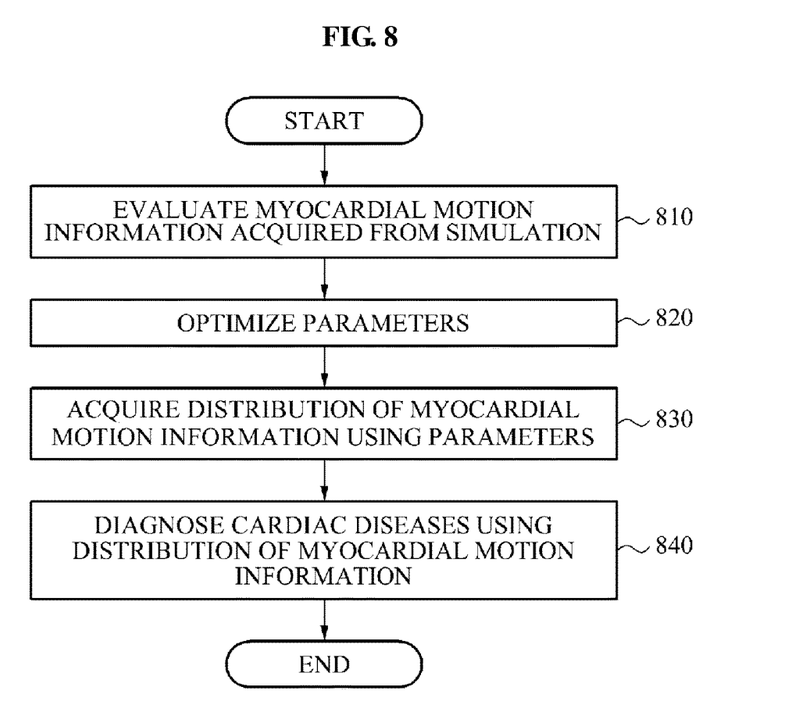
FIG. 8 is a flow chart illustrating an example of a method of modeling a cardiac motion.

FIG. 8 illustrates an example of a method of modeling a cardiac motion.

Referring to FIG. 8, in 810, a modeling apparatus may evaluate myocardial motion information acquired as a result of the modeling of 240. The myocardial motion information may include distribution of a myocardial strain and a myocardial stress.

In 810, the modeling apparatus may evaluate the myocardial motion information using the reference strain. For example, the reference strain may include cardiac motion information, for example the longitudinal strain, of the heart acquired from a 2D cardiac ultrasound image.

In 820, the modeling apparatus may optimize selected parameters so that the parameters reflect physical characteristics of the cardiac motion of the user using a result of the evaluation of 810. Here, the parameters may reflect the aforementioned physical characteristics of the cardiac motion. In 820, the modeling apparatus may analyze influences of the parameters with respect to the reference strain, and optimize the parameters using the analysis result.

According to an embodiment, using the result of the modeling of 240, the parameters applying the physical characteristics of the cardiac motion during production of the 3D heart shape model may be optimized to reflect the physical characteristics of the cardiac motion of the user.

In 830, the modeling apparatus may acquire the distribution of the myocardial motion information with respect to the entire heart using the parameters optimized in 820.

In 840, the modeling apparatus may diagnose one or more cardiac diseases using the distribution of the myocardial motion information acquired in 830.

Figure 9:
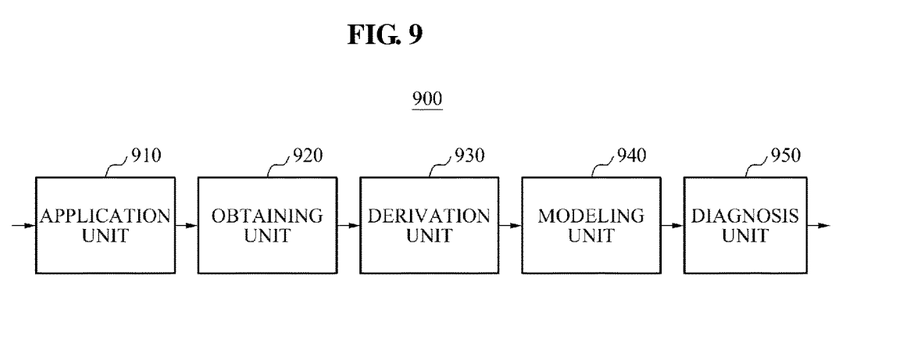
FIG. 9 is a block diagram illustrating an example of an apparatus for modeling a cardiac motion.

FIG. 9 illustrates an example of an apparatus 900 for modeling a cardiac motion.

Referring to FIG. 9, the apparatus 900 for diagnosing cardiac diseases, which may be referred to as a modeling apparatus, may include, for example, an application unit 910, an obtaining unit 920, a derivation unit 930, a modeling unit 940, and a diagnosis unit 950.

The application unit 910 may apply physical characteristics of a cardiac motion to a 3D heart shape model specialized for a user. The term "physical characteristics of a cardiac motion" refers to physical characteristics to be considered with respect to the cardiac motion, such as a fiber orientation, a passive stress of a myocardium, an active stress of the myocardium, and the like. The physical characteristics may be parameterized.

The application unit 910 may select parameters capable of reflecting the physical characteristics of the cardiac motion, and apply the physical characteristics to the heart shape model using the selected parameters.

The obtaining unit 920 may obtain a plurality of cardiac ultrasound images according to a temporal change so as to obtain a dynamic image.

The derivation unit 930 may derive a boundary condition by fusing the 3D heart shape model to which the physical characteristics of the cardiac motion are applied and the plurality of cardiac ultrasound images.

The boundary condition relates to a method of processing boundary regions or boundary spots between two different images being fused. The boundary condition may be divided into a displacement boundary condition and a load boundary condition. For example, the displacement boundary condition may indicate a motion in which feature points of the heart slide on a diaphragm in the cardiac ultrasound image. That is, the displacement boundary condition may indicate a physical change of respective positions of a myocardium. The load boundary condition may refer to a force or pressure applied to the respective positions of the myocardium inside the heart.

The modeling unit 940 may model the cardiac motion of the user using the boundary condition derived by the derivation unit 930.

The diagnosis unit 950 may diagnose the cardiac diseases using the modeling result of the modeling unit 940. A method of diagnosing the one or more types of cardiac diseases using the modeling result by the diagnosis unit 950 may refer to the description of FIG. 8.

Figure 10:
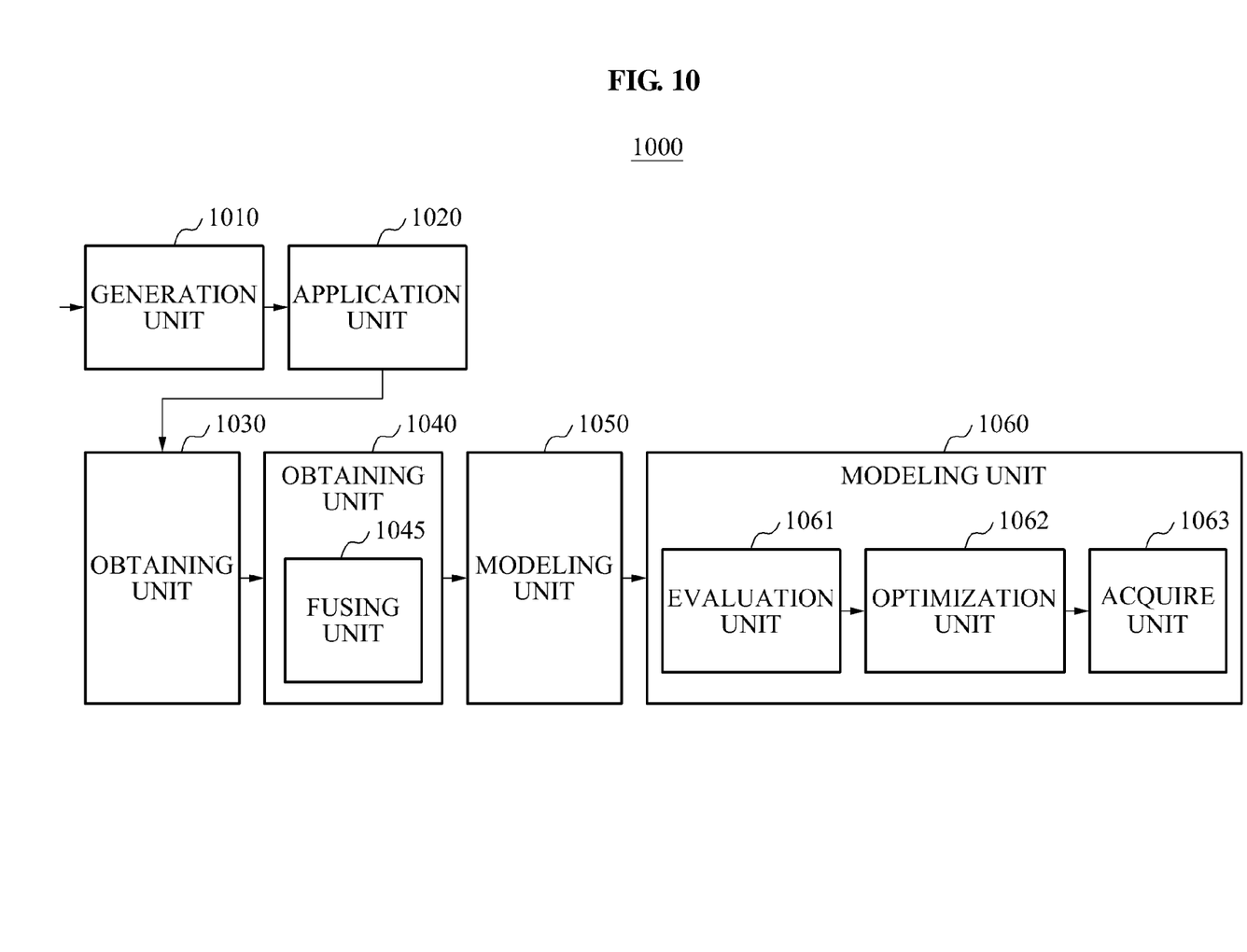
FIG. 10 is a block diagram illustrating another example of an apparatus for modeling a cardiac motion.

FIG. 10 illustrates an apparatus 1000 for modeling a cardiac motion.

Referring to FIG. 10, the modeling apparatus 1000 may include, for example, a generation unit 1010, an application unit 1020, an obtaining unit 1030, a derivation unit 1040, a modeling unit 1050, and a diagnosis unit 1060.

The generation unit 1010 may generate a 3D heart shape model specialized for a user based on a CT image capturing the user.

The application unit 1020 may apply physical characteristics of a cardiac motion to the specialized 3D heart shape model generated by the generation unit 1010.

The obtaining unit 1030 may obtain a plurality of cardiac ultrasound images according to a temporal change to obtain a dynamic image.

The derivation unit 1040 may derive a boundary condition by fusing the 3D heart shape model to which the physical characteristics of the cardiac motion are applied and the plurality of cardiac ultrasound images.

The derivation unit 1040 may include a fusing unit 1045 configured to fuse the 3D heart shape model of the user and the cardiac ultrasound image of the user. The fusing unit 1045 may fuse the 3D heart shape model and the cardiac ultrasound image, in consideration of a position change of feature points according to time in the 2D cardiac ultrasound image.

The modeling unit 1050 may model the cardiac motion of the user using the boundary condition derived by the derivation unit 1040.

The diagnosis unit 1060 may diagnose the cardiac diseases using the modeling result of the modeling unit 1050. The diagnosis unit 1060 may include an evaluation unit 1061, an optimization unit 1062, and an acquiring unit 1063.

The evaluation unit 1061 may evaluate the myocardial motion information acquired by the modeling of the modeling unit 1050. The diagnosis unit 1060 may optimize parameters using the evaluation result of the evaluation unit 1061, so that the parameters reflect physical characteristics of the cardiac motion of the user.

The optimization unit 1062 may optimize the parameters using the modeling result of the modeling result 1050, so that the parameters reflect physical characteristics of the cardiac motion of the user. The optimization unit 1062 may perform the optimization by analyzing sensitivity of main parameters according to the modeling result and updating the parameters.

The acquiring unit 1063 may acquire distribution of myocardial motion information related to the entire heart of the user using the optimized main parameters. The diagnosis unit 1060 may diagnose the cardiac diseases using distribution of the distribution of myocardial motion information.

The units described herein may be implemented using hardware components, software components, or a combination thereof. For example, a processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums.

The above-described embodiments may be recorded, stored, or fixed in one or more non-transitory computer-readable media that includes program instructions to be implemented by a computer to cause a processor to execute or perform the program instructions. The media may also include, alone or in combination with the program instructions, data files, data structures, and the like. The program instructions recorded on the media may be those specially designed and constructed, or they may be of the kind well-known and available to those having skill in the computer software arts. Examples of non-transitory computer-readable media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, and the like.

Examples of program instructions include both machine code, such as produced by a compiler, and files containing higher level code that may be executed by the computer using an interpreter. The described hardware devices may be configured to act as one or more software modules in order to perform the operations and methods described above, or vice versa. Any one or more of the software modules described herein may be executed by a dedicated hardware-based computer or processor unique to that unit or by a hardware-based computer or processor common to one or more of the modules. The described methods may be executed on a general purpose computer or processor or may be executed on a particular machine such as the apparatus for diagnosing cardiac diseases described herein.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A method of modeling a cardiac motion to generate a patient heart model, the method comprising:
   generating, by way of a processor, a 3-dimensional (3D) heart shape model;
   applying physical characteristics of a patient cardiac motion to the 3D heart shape model;
   obtaining, via a medical imaging device, cardiac ultrasound images according to a temporal change;
   obtaining a reference strain based on the cardiac ultrasound images;
   deriving a boundary condition by fusing the 3D heart shape model to which the physical characteristics are applied and the cardiac ultrasound images based on a position change of feature points over time in the cardiac ultrasound images;
   constructing the patient heart model and acquiring motion information by modeling the patient cardiac motion using the boundary condition;
   comparing the motion information and the reference strain;
   optimizing parameters reflecting the physical characteristics of the patient cardiac motion based on a result of the comparison; and
   diagnosing a cardiac disease based on the distribution of the motion information obtained using the optimized parameters.

2. The method of claim 1, wherein the 3D heart shape model is generated based on a 2D image or 3D image capturing a user.

3. The method of claim 2, wherein the 2D image or 3D image capturing the user comprises a computed tomography (CT) image.

4. The method of claim 1, wherein the applying comprises:
   selecting parameters reflecting the physical characteristics of the patient cardiac motion; and
   applying the physical characteristics of the patient cardiac motion to the 3D heart shape model using the parameters.

5. The method of claim 4,
   wherein the diagnosing comprises:
   optimizing the selected parameters using the result of the modeling; and
   acquiring distribution of myocardial motion information using the optimized parameters.

6. The method of claim 5, wherein the optimizing comprises:
   evaluating the myocardial motion information acquired as a result of the modeling; and
   optimizing the selected parameters using a result of the evaluation so that the parameters reflect physical characteristics of the patient cardiac motion.

7. The method of claim 6, wherein the myocardial motion information comprises a strain distribution of a myocardium and a stress of the myocardium.

8. The method of claim 6, wherein the evaluating comprises:
   evaluating the myocardial motion information using the reference strain.

9. The method of claim 8, wherein the reference strain comprises patient cardiac motion information acquired from the cardiac ultrasound images.

10. The method of claim 8, wherein the optimizing comprises:
    analyzing an influence of the parameters with respect to the reference strain; and
    optimizing the parameters using a result of the analysis.

11. The method of claim 1, wherein the physical characteristics comprise at least one of a fiber orientation of a myocardium, a passive stress of the myocardium, and an active stress of the myocardium.

12. The method of claim 1, wherein the deriving further comprises:
    searching for a displacement boundary condition of the boundary condition using the 3D heart shape model and the cardiac ultrasound images being fused.

13. The method of claim 1, wherein the boundary condition comprises at least one of a displacement boundary condition and a load boundary condition.

14. A non-transitory computer-readable medium storing instructions that, when executed by one or more processors, cause the one or more processors to implement a method comprising:
    generating a 3-dimensional (3D) heart shape model;
    applying physical characteristics of a patient cardiac motion to the 3D heart shape model;
    retrieving cardiac ultrasound images obtained according to a temporal change;
    obtaining a reference strain based on the cardiac ultrasound images;
    deriving a boundary condition by fusing the 3D heart shape model to which the physical characteristics are applied and the cardiac ultrasound images based on a position change of feature points over time in the cardiac ultrasound images;
    constructing the patient heart model and acquiring motion information by modeling the patient cardiac motion using the boundary condition;
    comparing the motion information and the reference strain;
    optimizing parameters reflecting the physical characteristics of the patient cardiac motion based on a result of the comparison; and
    diagnosing a cardiac disease based on the distribution of the motion information obtained using the optimized parameters.

15. An apparatus for diagnosing cardiac diseases to generate a patient heart model, the apparatus comprising:
    a medical imaging device configured to obtain cardiac ultrasound images according to a temporal change; and
    one or more processors configured to:
    obtain a reference strain based on the cardiac ultrasound images;
    apply physical characteristics of a patient cardiac motion to a 3-dimensional (3D) heart shape model;
    derive a boundary condition by fusing the 3D heart shape model to which the physical characteristics are applied and the obtained cardiac ultrasound images in consideration of a position change of feature points according to time in the cardiac ultrasound images;
    construct the patient heart model and acquiring motion information by modeling the patient cardiac motion using the boundary condition;
    compare the motion information and the reference strain;
    optimize parameters reflecting the physical characteristics of the patient cardiac motion based on a result of the comparison; and diagnose a cardiac disease based on the distribution of the motion information obtained using the optimized parameters.

16. The apparatus of claim 15, wherein, to perform the applying of the physical characteristics, the one or more processors is configured to select parameters reflecting the physical characteristics of the patient cardiac motion and apply the physical characteristics to the 3D heart shape model using the parameters.

17. The apparatus of claim 16, wherein the one or more processors is further configured to:
acquire a distribution of myocardial motion information using the optimized parameters,
wherein the performing of the diagnosing includes performing the diagnosing for the cardiac diseases using the distribution.

18. The apparatus of claim 17, wherein, to perform the diagnosing for the cardiac diseases, the one or more processors are further configured to evaluate myocardial motion information acquired from the result of the modeling, and optimize the parameters using a result of the evaluation so that the parameters reflect physical characteristics of the patient cardiac motion.

19. The apparatus of claim 16, wherein the one or more processors are further configured to perform the obtaining of the cardiac ultrasound images according to the temporal change.

* * * * *